United States Patent [19]

Coombes

[11] 3,963,697
[45] June 15, 1976

[54] LABELLED CARDIOTONIC GLYCOSIDES FOR USE IN RADIOIMMUNOASSAY

[75] Inventor: Robert F. Coombes, La Habra, Calif.

[73] Assignee: Curtis Nuclear Corporation, Los Angeles, Calif.

[22] Filed: Aug. 29, 1974

[21] Appl. No.: 501,619

[52] U.S. Cl.............................. 260/210.5; 424/182
[51] Int. Cl.²......................................... C07J 19/00
[58] Field of Search..................... 260/210.5, 211 R; 424/1

[56] References Cited
UNITED STATES PATENTS 3,843,628   8/1974   Minato............................ 260/210.5

OTHER PUBLICATIONS

Chem. Abstracts, vol. 80, No. 1-2, "*PharmacoDynamics*", 10141 N, 1974.
Analytical Chemistry, "*Radioimmunoassay*", vol. 45, No. 11, p. 882, Sept. 1973.
Morrison and Boyd, "*Organic Chemistry*", Allyn & Bacon, Inc., Boston, 1966, p. 360.

*Primary Examiner*—Elbert L. Roberts
*Assistant Examiner*—Cary Owens
*Attorney, Agent, or Firm*—Lyon & Lyon

[57] ABSTRACT

Disclosed are radioactive cardiotonic glycosides and a process of making such glycosides, the compounds being useful for radioimmunoassay of body fluids for cardiotonic glycoside content.

The novel synthesis comprises reaction of a hydroxyl group of the sugar with a dicarboxylic acid derivative such as a diacid, diacid anhydride or a diacyl halide and thereafter reacting the free carboxylic group with a compound which will undergo electrophilic substitution reactions. A radioactive isotope, preferably $^{125}I$, is reacted via electrophilic substitution with the compound to form the radioactive cardiotonic glycoside.

21 Claims, No Drawings

LABELLED CARDIOTONIC GLYCOSIDES FOR USE IN RADIOIMMUNOASSAY

BACKGROUND OF THE INVENTION

The use of various steroids to increase the intensity of the heartbeat is known. A number of steroid glycosides have been found useful in cardiotherapy, but the corresponding aglycons (genins), which share the characteristic steroid structure of the glycosides are convulsive poisons.

For purposes of definition, a cardiotonic glycoside is one which increases the intensity of the heart beat but may decrease the rate of heartbeat. These glycosides may be designated by the following general formula:

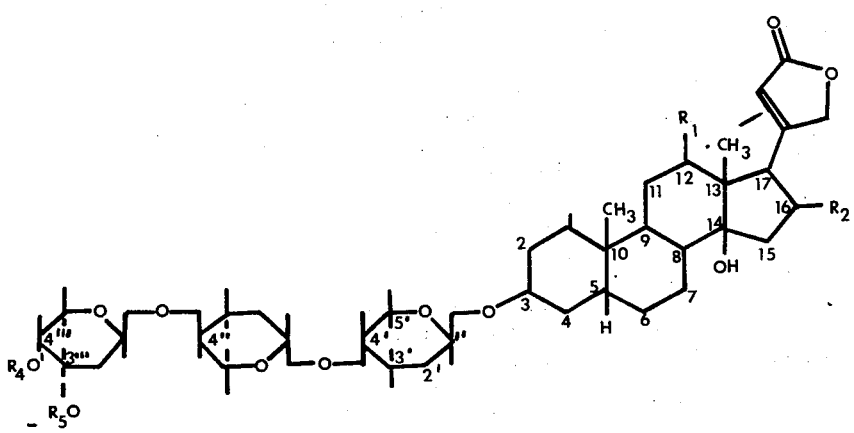

The corresponding aglycons have a hydroxy group at position 3 rather than a glycoside conjugate.

A wide number of sugars may be employed to form cardiotonic glycosides, as long as the steroid nucleus is a cardenolide which contains a five membered lactone ring at the $C_{17}$ position. Particular cardiotonic glycosides useful in the treating of heart disceases and which are readily available include digoxin, digitoxin and gitoxin. These compounds differ at the $C_{12}$ and $C_{16}$ position of the steroid ($R_1$ and $R_2$), in that digitoxin contains a hydrogen substituent at each position, digoxin contains a hydroxyl at $C_{12}$ and a hydrogen at $C_{16}$ while gitoxin contains a hydrogen at $C_{12}$ and hydroxyl at $C_{16}$. The glycoside portion of each of these compounds comprises three digitoxose sugars. The $3'$, $3''$, $3'''$ and $4'''$ positions bear hydroxyl groups while the $5'$, $5''$ and $5'''$ bear methyl substituents. Other sugars which may be found in cardiotonic glycosides include the lanatoside series which differs from the digitoxose in that the $3'''$ position bears an acetyl while the $4'''$ position contains an additional glucose sugar. When this glycoside is conjugated to digoxigenin it is designated lanatoside A, while if it is conjugated with gitoxigenin it is designated lanatoside B, and if it is conjugated with digitoxigenin it is designated lanatoside C.

Other sugar units which may give a compound which has cardiotonic activity, when they are conjugated to a cardenolide steroid, include rhamnose, antiarose, digitalose, thevetose, talomethylose, cymarose, oleandrose, sarmentose, boivinose and diginose. By combining three of these units with an aglycon, various cardiotonic glycosides may be formed. The aglycons alone are usually convulsive poisons not useful in medicine. For a more thorough discussion of cardiotonic glycosides and aglycons, see "Rodd's Chemistry of Carbon Compounds", Second Edition, Vol. 2, part D, chapter 17, and "Chemistry and Metabolism of Digitalis", *Digitalis*, edited by Charles Fisch and Borys Furawicz, Grune & Stratton, Inc., New York, 1969.

As previously mentioned, although the glycosides have been found to exhibit much less toxicity than the corresponding aglycon, in many instances the difference between a therapeutic and a toxic dose of a glycoside is only in the order of a few micrograms per kilogram of blood. Digitalis intoxication occurs frequently due to the small differences between therapeutic and toxic quantities. The therapeutic quantity of any cardiotonic glycoside cannot be predicted in advance of medication since each patient may react differently to the dosage, and retain different quantities of the drug in the blood stream.

Digitalis intoxication occurs with increasing frequency in elderly heart patients, since diseased renal function in the aged can result in higher and sometimes toxic levels of cardiotonic glycoside residue in the blood. Also, there may be some overlapping between therapeutic and toxic blood levels due to susceptability of the myocardium to digitalis. For example, the patient whose myocardium is diseased may show signs of toxicity despite therapeutic blood levels. Other clinical conditions contributing to digitalis intoxication are coronary ischemia and potassium depletion. The problems of digitalis intoxication are compounded in that its symptoms may often be mistaken for fatigue or restlessness.

Generally, accepted therapeutic levels for digoxin range from 0.8 to 2.4 ng/ml while toxic levels range from 2.1 to 8.7 ng/ml Toxic versus non-toxic levels of digitoxin also overlap, i.e., 3.0 to 39.0 ng/ml may be therapeutic while 26.0 to 43.0 ng/ml may be toxic. Higher levels of digoxin and digitoxin are generally lethal.

Radioimmunoassay for cardiotonic glycosides has proved extremely effective in detecting under-medicated, adequately medicated and over-medicated or toxic levels of the drug in blood serum. That sampling technique comprises the use of a radioactive steroid glycoside or aglycon and an antibody which will bind both the radioactive steroid and the cardiotonic glycoside in the blood on a competitive basis. By counting the amount of radioactive material reacting with the antibody, the amount of cardiotonic glycoside in the blood may be calculated. From the results, it can be quickly determined whether the patient has been undermedicated, properly medicated or over-medicated and is suffering digoxin toxicity.

For radio labelling of steroids, 125-Iodine or 131-Iodine are preferred, since they exhibit high specific activity, while $^{14}C$ and $^3H$ are also available. The use of compounds exhibiting a high specific activity permits the use of considerably less material for the same counting efficiency. Counting with such isotopes can be achieved by liquid scintillation or gamma ray spectroscopy counting procedures.

The sampling procedure preferably consists of the use of an antibody polymer in tablet form, which antibody has been raised in an animal host by the administration of an appropriate antigen. The radioactive steroid and the cardiotonic glycoside isolated in the blood serum then complete with each other for a limited number of binding sites on the antibody to form an insoluble complex. The antigen/antibody complex is then separated via centrifuge techniques and the radioactive portion is measured, as for example, by gamma counter. From the difference in radioactivity in the test specimen, compared to standards of known cardiotonic glycoside concentrations in blood, the level of cardiotonic glycoside in the test sample may be accurately computed.

For a more complete discussion of radioimmunoassay principles, see A. R. Midgday, Jr. and G. D. Niswender, in "Karolinska Symposia on Research Methods in Endocrinology, 2nd Symposium: Steroid Assay by Protein Binding," The Reproductive Endocrinology Research Unit, Stockholm (1970), 320-333 and W. D. Odell and W. H. Daughadey, "Principles of Competitive Protein-Binding Assays," J. B. Lippincott Company, Philadelphia (1971). For a complete discussion on the preparation of protein-digoxin conjugates necessary for the production of antibodies, see "Digoxin-Specific Antibodies", Butler et al., Proc. Natl. Acad. Sci. U.S. 57:71.

The method most commonly used in conjugating a radioactive isotope, such as 125-Iodine, to a steroid is via an electrophilic substitution reaction. Because of the high susceptability of phenol derivatives to electrophilic substitution, since the hydroxyl is an activating group, radioactive steroids have been synthesized by conjugating tyrosine or tyrosine methyl ester (TME) onto the steroid, after which the compound may be reacted with the radioactive isotope ($^{125}$I).

Oliver et al., Journal of Clinical Investigation, 47, 1035 (1968) teach the synthesis of a digitoxigenin-3-0-succinyl-iodine-125 tyrosine methyl ester for use in cardiotonic glycoside radioimmunoassay procedures. Such a compound, although suitable for measuring the level of the drug in blood serum, suffers from the disadvantage that it is extremely difficult and expensive to produce. The succinylation step of the $C_3$-hydroxyl group of the genin, which is used at the binding site for the TME and iodine-125, proceeds very slowly and may require reaction time on the order of months. It is believed that the slow reaction time associated with the succinylation of the $C_3$-hydroxyl, is due to the fact the $C_3$-hydroxyl group is fixed in an axial position and offers a large amount of steric hindrance. Additionally, although such a reaction procedure is suitable for the synthesis of digitoxigenin derivatives, where the $C_{12}$ substituent is a hydrogen, it is not per se suitable for the synthesis of radioactive digoxigenin derivatives. Digoxigenin has at the $C_{12}$ position and equatorial hydroxyl substituent which will more readily be succinylated than the axial-3-hydroxyl group, since it offers less steric hindrance. Thus succinylation of the 3-hydroxyl of the genin not only proceeds slowly but for many compounds produces little or no yield of a useful immunoreactive derivative unless other positions are blocked. In addition, Stall et al., "The Specificity of the Digoxin Radioimmunoassay Procedure", *Res. Commun. Chem. Pathol Pharmacol*, 4, 503 (1972) shows that digoxigenin has a lower affinity for antibody than digoxin itself. They show a crossreactivity of about 34% wherein the optimum ratio of binding ability of radiolabelled to unlabelled antigen should be 1:1. Thus it would be expected that a radioactive glycoside will bind on a more competitive basis with an antibody than the corresponding aglycon.

Although Draws et al., "Faster and Easier Radioimmunoassay of Digoxin," *Clinical Chemistry*, Vol. 20, No. 3, 343-347 (1974) discusses the use of a $^{125}$I-tyrosine methyl ester of digoxin, there is no indication that such a compound should be a sugar hydroxyl substituted material or any indication of how such a compound might be synthesized.

It is an object of this invention to provide a process of synthesizing a radioactive steroid which will complete on a predictable basis for sites on an antibody with cardiotonic glycosides to be measured.

It is another object of this invention to provide a process of synthesizing such radioimmunoassay compounds via an improved and simplified procedure.

It is yet another object of this invention to provide a radioimmunoassay compound having a high specific activity and improved stability upon storage.

SUMMARY OF THE INVENTION

These and other objects are accomplished by reacting a steroid glycoside of the general formula:

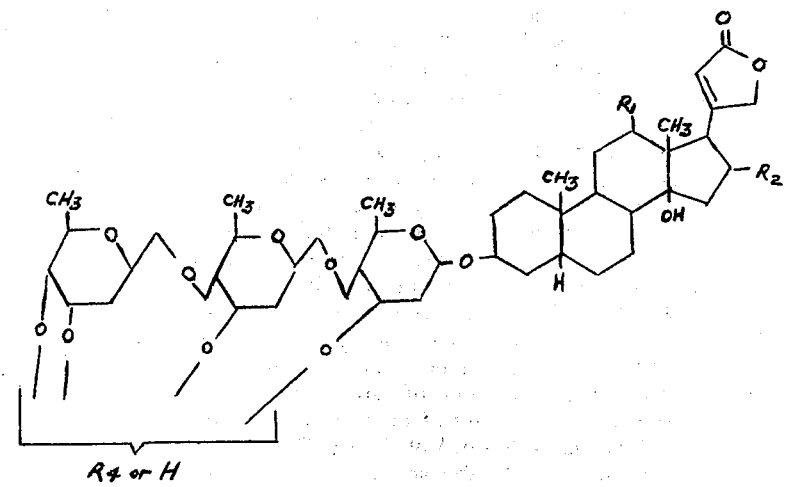

wherein $R_1$ and $R_2$ are selected from the group consisting of hydrogen or hydroxyl and $R_4$ is a diacid derivative, giving the corresponding steroid glycoside derivative in which one or more sugar hydroxyl groups have been acylated, each being acylated with only one acyl group of each diacid, leaving the other acyl group free for further reaction. Then, further reacting with the remaining unesterified acyl group, a compound which will readily undergo electrophilic substitution to yield the corresponding disubstituted dicarboxylic acid derivative. The resulting compound is then reacted via electrophilic substitution with a radioactive isotope.

PREFERRED EMBODIMENT

The following reaction scheme is preferably used in synthesizing the radioimmunoassay compounds of this invention:

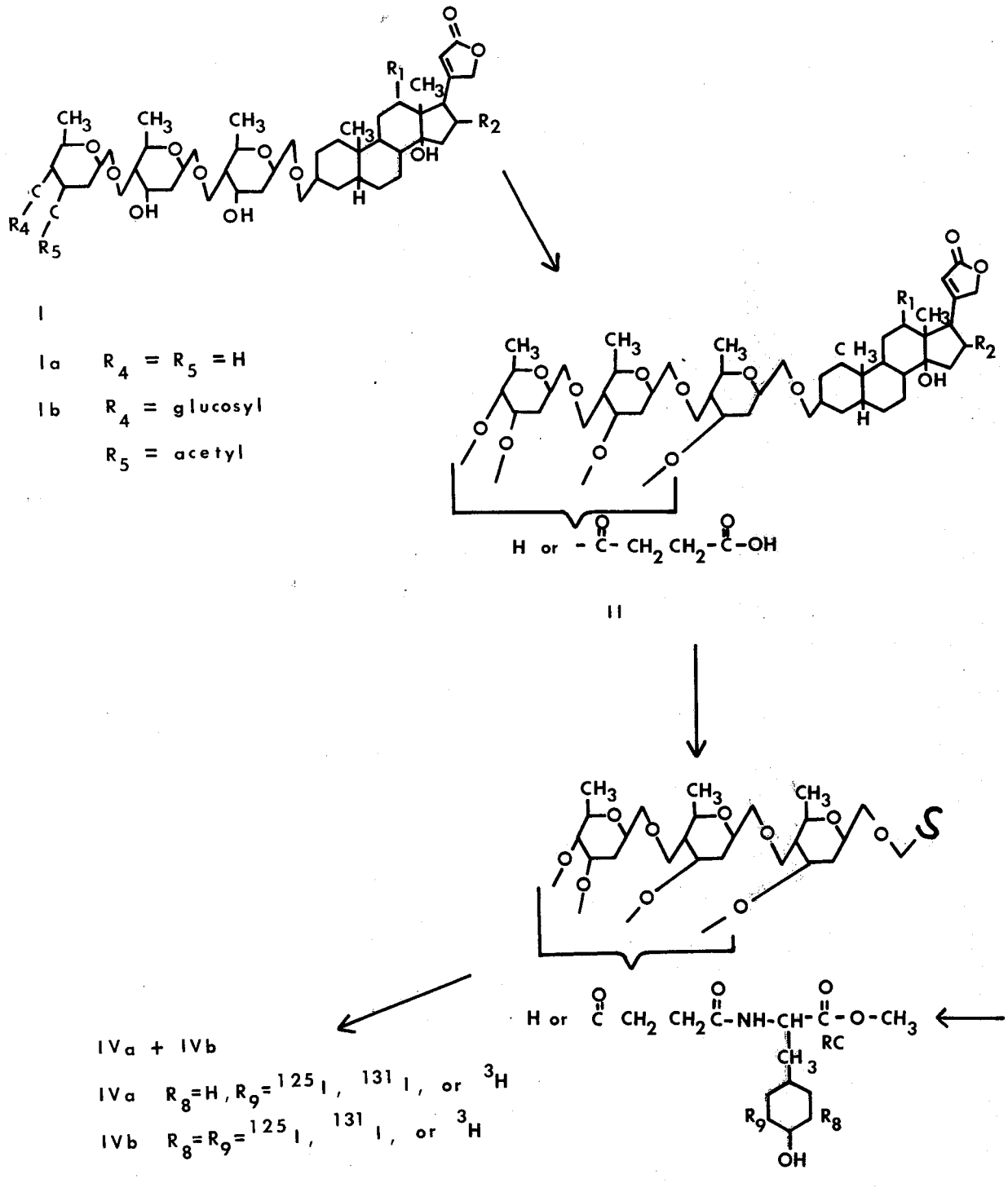

Compound I is a cardiotonic glycoside wherein the cardenolide steroid portion is either a derivative of digoxin wherein $R_1$ is OH and $R_2$ is H, digitoxin wherein $R_1$ and $R_2$ are H, or gitoxin wherein $R_1$ is H and $R_2$ is OH. The sugar portion substituted at the 3-position of the steroid portion may be any glycoside which bears a primary or a secondary hydroxyl group. Prefereably, as shown in structure Ia, three digitose sugars are employed as the glycoside portion, wherein $R_4$ and $R_5$ are hydrogens. A diacid, diacid anhydride or diacid halide is reacted at sugar hydroxyl groups of Ia, particularly those which occupy the less hindered equatorial configuration and those on the less hindered terminal sugar. It is believed that a combination of compounds, predominately 3'''- and 4'''- monosubstituted compounds are obtained via this reaction. The 4'''-position is predominately equatorial. The 3'''-position is more often in equatorial configuration than the 3''- or 3'- hydroxyl groups, and it can also be acylated via migration of an acyl group from the 4'''-position. The 3'-and 3''-hydroxyl groups are predominately axial, more hindered due to greater substitution on these sugars, and not available to acylation via molecular rearrangement.

Lanatoside A (digitoxin analog), lanatoside B (gitoxin analog) and lanatoside C (digoxin analog) may also be employed. These compounds are shown in structure Ib, wherein $R_4$ is a glucosyl and $R_5$ is an acetyl. A diacid, diacid anhydride, or diacid halide is reacted at the primary 5''''-hydroxyl group and also at the secondary 2'''', 3'''' and/or 4'''' hydroxyl groups, which are all predominantly equatorial.

Compound II is a cardiac glycoside with a succinylated sugar hydroxyl group. It will be understood that a variety of bifunctional acylating agents may be employed in accordance with this invention although succinic anhydride and glutaric anhydride are preferred. Other diacylating agents which may be used to acylate the sugar hydroxyl groups are carbonic acid, oxalic acid, malonic acid, adipic acid, pimelic acid, maleic acid, phthalic acid, and more preferably anhydrides of these acids. Also, acid halides may be employed, e.g. phosgene. In addition, such acids as 3-(p-hydroxyphenyl) propionic acid or N-succinyl tyrosine or reactive intermediates prepared from these, such as anhydrides, may be used to attach in one step a compound which is activated towards electrophilic substitution. Compound II is a succinyl cardiotonic glycoside, as for example, 4'''-succinyl digoxin. The free carboxyl groups of compound II are then reacted with an aromatic compound having an activating substituent on the ring so the ring will readily undergo electrophilic substitution. Most suited are substituted phenols or aromatic amines. For example, tyrosine, and preferably a tyrosine derivative with a blocked carboxyl group, such as tyrosine methyl ester, have been employed since they readily undergo electrophilic substitution. However, other compounds may also be employed, for example compounds which contain an imidazole group, such as the amino acid histidine.

Compound III is a succinyl cardiotonic glycoside tyrosine methyl ester wherein S is an abbreviation for the cardenolide steroid portion of the molecule. The sites, indicated by $R_8$ and $R_9$, which are ortho to the hydroxyl group of the phenol, are the preferred sites for electrophilic substitution.

Compound VI is the final, radioimmunoassay compound of this invention, a radio-isotope such as $^{125}I$ having been substituted onto the phenol ring shown in compound III.

The invention is further illustrated by references to the examples of preferred embodiments which follow.

EXAMPLE I

Synthesis of Succinyl Digitoxin

Succinic anhydride, 9g, was stirred for 30 minutes with 50 ml of pyridine which had previously been dried over molecular sieves (Linde 3A). To 1g of digitoxin in a 4 oz. glass stoppered bottle was added 50 ml of this concentrated solution of succinic anhydride in pyridine. The mixture was heated at 85°C in an oil bath for 90 minutes with the stopper in. The solution was allowed to cool, and then it was mixed with 50g of cracked ice. Thirty minutes later the volume was brought to 200 ml with water, and the solution was evaporated to dryness in vacuum. The residue was extracted with water (2 × 160 ml) to remove most of the succinic acid. The remaining material was purified by preparative layer chromatography on 20 cm × 20 cm × 2 mm silica gel, using 1:7 methanol-chloroform. The main product band was eluted with ethanol and dried in vacuum to give 509 mg of succinyl digitoxin: $\lambda$ max 218nm (ethanol); TLC, slower $R_f$ than digitoxin (1:7 methanol-chloroform).

EXAMPLE II

Synthesis of Succinyl Digitoxin Tyrosine Methyl Ester

To the 509 mg of succinyl digitoxin of Example I was added 139 mg of tyrosine methyl ester hydrochloride (TME) and 330 mg of dicyclohexyl-carbodiimide (DCC) in 6 ml of pyridine (previously dried over molecular sieves). The reaction vial was capped and protected from light and set aside at room temperature. Three days later the solution was poured into 120 ml of water, and this mixture was shaken thoroughly. The supernate was separated by centrifugation and discarded. The residue was evaporated with methanol in aspirator vacuum, and then it was subjected to high vacuum in order to remove most of the pyridine. This crude product was purified by preparative layer chromatography on 20 cm × 20cm × 2 mm silica gel, using 1:7 methanol-chloroform. The main product band was eluted with ethanol and dried in vacuum to give 250 mg of Succinyl Digitoxin Tyrosine Methyl Ester: $\lambda_1$ max = 278 nm (ethanol) $\lambda_2$ max=222.5 nm $\epsilon_{278}$ = 1620 $M^{-1}$ (theoretical 1680 $M^{-1}$), UV spectrum was identical to that of a mixture of digitoxin and TME (1:1 molar ratio); TLC, faster $R_f$ than digitoxin, TME, or succinyl digitoxin (1:7 methanol-chloroform).

EXAMPLE III

Synthesis of $^{125}I$-(Succinyl Digitoxin Tyrosine Methyl Ester)

About 2 mg of succinyl digitoxin tyrosine methyl ester was re-purified by TLC on 50 × 80 × 0.25 mm of silica gel, using 1:9 methanol-chloroform. The desired comperend was eluted with ethanol, and this was diluted to give an O.D. of 0.150 at 278 mm (93 μg/ml). To a 10 × 75 mm test tube which contained an 8 mm stirring bar was added 25 μl of this solution (2.37 μg of succinyl digitoxin tyrosine methyl ester), 75 μl of 0.5M pH 7.6 phosphate buffer, and 25 μl (6 mCi) of Na $^{125}$I. To the stirred solution was added 25 μl of 0.4% chloramine T in 0.05M pH 7.6 phosphate buffer. Exactly two minutes later was added 25 μl of 0.4% sodium metabisulfite in 0.05M pH 7.6 phosphate buffer. Two minutes later the reaction solution was transferred to a vial containing 1g of strong base ion exchange resin, chloride form, 30–50 mesh, and 10 ml of 100% ethanol. The vial was rotate mixed for 10 minutes, centrifuged at 3000 rpm for five minutes, and the supernate was transferred to 290 ml of 0.5% albumin, 0.9% sodium chloride, 0.001% tetrocycline hydrochloride. Yield was 3.65 mCi of $^{125}$I-(succinyl digitoxin tyrosine methyl ester).

This isotopic tracer was immunoreactive but not ideally suited to our methodology because of considerable nonspecific adsorption to some of the insoluble constituents of our antibody polymer tablets.

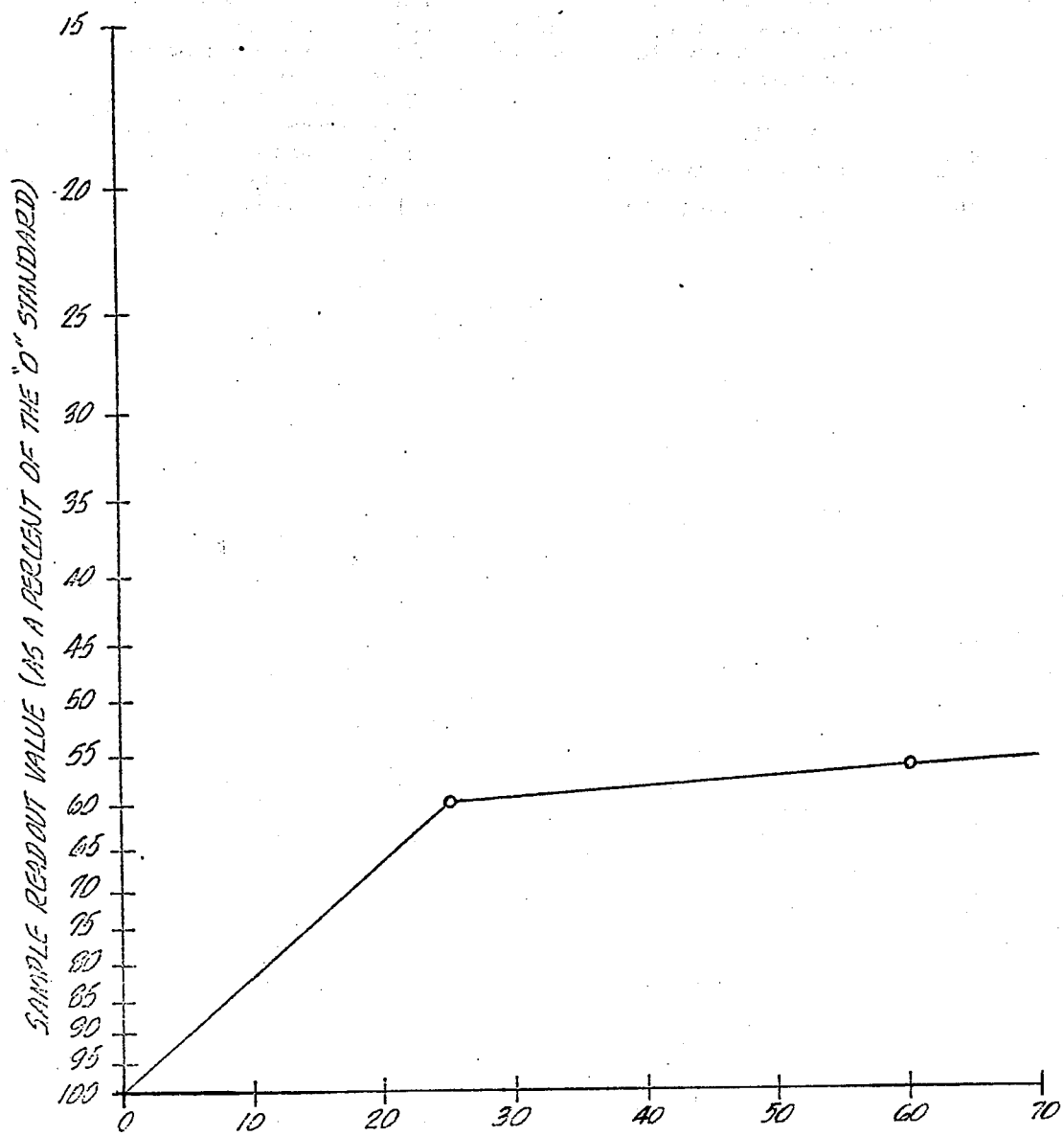

EXAMPLE IV

Synthesis of Succinyl Digitoxin Tyrosine

Ten milligrams of succinyl digitoxin tyrosine methyl ester was dispersed by sonication in 10 ml of 0.025 M phosphate buffer, pH 7.6. Chymotrypsin, 12 mg, was added and the slurry was rotate mixed at room temperature. After two days another 12 mg of chymotrypsin was added, and the rotate mixing was continued for a total of four days. The mixture was evaporated to dryness, and the residue was taken up in methyl alcohol. Insoluble material was removed by centrifugation, and the supernate was purified by thin layer chromatography on two 50 mm × 80 mm × 0.25 mm silica gel plates, using 1:3 methanol chloroform. The product was eluted with ethanol to give a spectrophotometrically determined yield of 4.96 mg (50%) of succinyl digitoxin tyrosine: TLC, much slower $R_f$ than the starting material or succinyl digitoxin.

EXAMPLE V

Synthesis of $^{125}$I-(Succinyl Digitoxin Tyrosine)

An ethanol solution succinyl digitoxin tyrosine was prepared with an optical density (O.D.) of 0.116 at 278mm. Twenty-five $\mu$l of this solution was added to a vial which contained 75$\lambda$ of 0.5M pH 7.6 phosphate buffer and 25$\lambda$ (2.3 mCi) of Na$^{125}$I. To the stirred solution was added 25$\lambda$ (100 $\mu$g) of chloramine T in 0.05 M phosphate buffer, pH 7.6. Exactly two minutes later was added 25$\lambda$(100 $\mu$g) of sodium meta-bisulfite in 0.05 M phosphate buffer, pH 7.6. The reaction solution was transferred to a vial which contained 0.5g of strong base resin, acetate form and 5 ml of ethanol. This vial was rotate mixed for five minutes, and the supernate was removed with a pasteur pipet and discarded. The desired product was eluted from the resin by rotate mixing for ten minutes with 5 ml of 4:1 (v/v) of ethanol-glacial acetic acid. The supernate was transferred to a bottle which contained 195 ml of 0.5% albumin, and the product was neutralized with about 15 ml of IN NaOH. The yield was 972 $\mu$Ci of $^{125}$I-succinyl digitoxin tyrosine.

The anionic $^{125}$I-(succinyl digitoxin tyrosine) had very little nonspecific absorption to insoluble components of our antibody polymer tablets, and it was therefore superior to the ester form of Example III for our particular methodology.

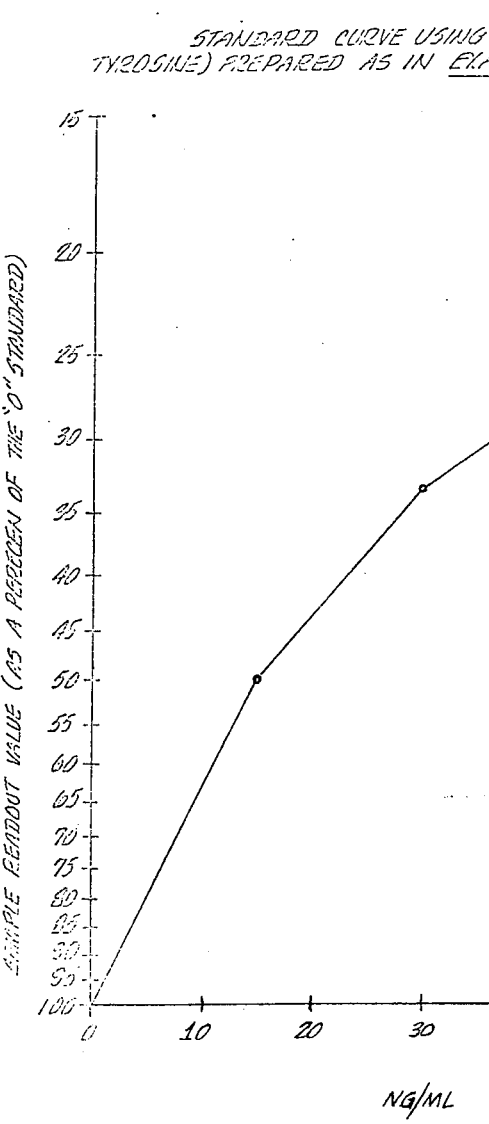

STANDARD CURVE USING $^{125}$I-(SUCCINYL DIGITOXIN TYROSINE) PREPARED AS IN EXAMPLE IV

EXAMPLE VI

Synthesis of Succinyl Digoxin

Succinic anhydride, 9g, was stirred for 30 minutes with 50 ml of pyridine which had previously been dried over molecular sieves. To 1g of digoxin in a 4 oz glass stoppered bottle was added the concentrated solution succinic anhydride in pyridine by decanting the supernate from the settled, undissolved succinic anhydride. The bottle was sealed with a glass stopper and heated in an oil bath at 85°–90° for 90 minutes. The reaction was allowed to cool to room temperature, and then about 50g of crushed ice was added. After 30 minutes, the mixture was evaporated to dryness in vacuum. The residue was washed into four "40 ml" centrifuge tubes with several portions of water. The tubes were centrifuged, and the supernate was discarded. The residue was again washed and centrifuged. The residue was then placed in methanol solution and evaporated to dryness in vacuum. The product was purified by preparative layer chromatography on 20 cm × 20 cm × 0.25 mm of silica gel, developing with 1:5 methanol-chloroform. The product was eluted with ethanol and dried in vacuum to give succinyl digoxin: $\lambda max=218$ nm (ethanol); TLC, slower $R_f$ than digoxin (1:7 methanol-chloroform).

EXAMPLE VII

Synthesis of Succinyl Digoxin Tyrosine Methyl Ester

This tyrosine methyl ester derivative was prepared from the compound of Example VI via the same procedure as the succinyl digitoxin tyrosine methyl ester of Example II.

EXAMPLE VIII

Synthesis of $^{125}$I-(Succinyl Digoxin Tyrosine Methyl Ester)

To a 12.5 × 105 mm vial containing an 8 mm stirring bar was added 25λ (0.6 µg) of ethanolic succinyl digoxin tyrosine methyl ester, 75λ of 0.5M pH 7.6 phosphate buffer, and 35λ (6.25 mCi) of Na $^{125}$I. To the stirred solution was added 25λ of 0.4% chloramine T in 0.05 M phosphate buffer. Exactly two minutes later was added 25λ of 0.4% sodium metabisulfite in 0.05M pH 7.6 phosphate buffer. Two minutes later the reaction solution was transferred to a 12.5 × 105 mm vial which contained 1g of Amberlite IRA-400 C.P. (chlorideform) anion exchange resin and 10 ml of 100% ethanol. The mixture was shaken for nine minutes (time of transfer from the reaction vial to the ion exchange vial was one minute). The vial was centrifuged for five minutes, and the liquid contents were transferred to a bottle containing 90 ml of 0.9% sodium chloride. This was diluted with 200 ml of a solution of 6g of bovine serum albumin in 0.9% sodim chloride. Yield was slightly over 1 mCi of $^{125}$I-(succinyl digoxin tyrosine methyl ester).

The specific activity was equal to or greater than 1670 µCi/µg based on weight of uniodinated succinyl digoxin tyrosine methyl ester used in the iodination. This is a much higher specific activity than is obtained by competitors using other process and derivatives.

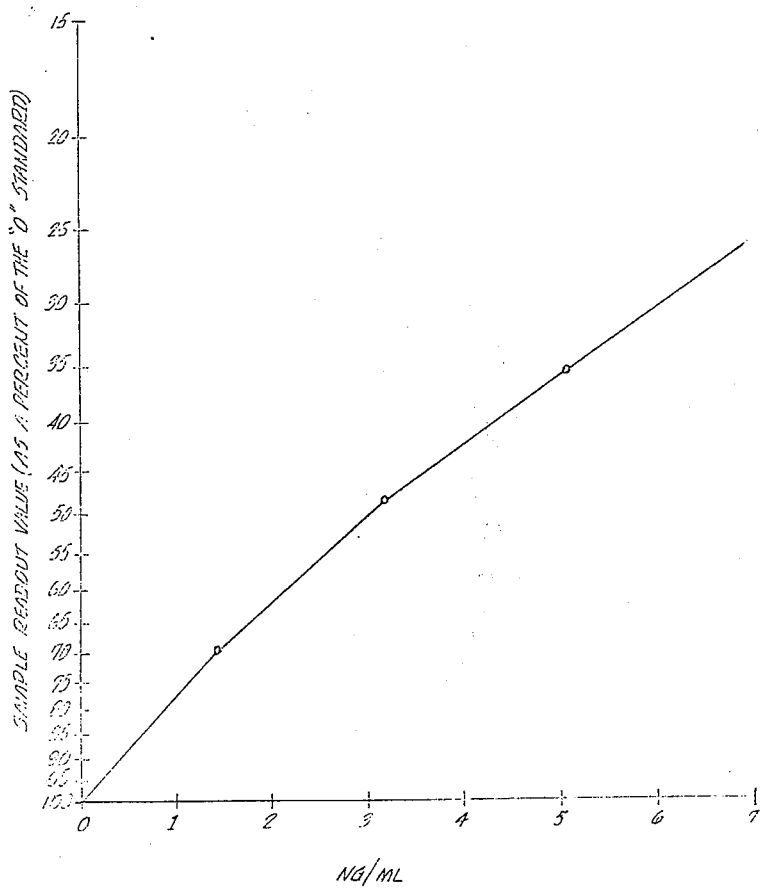

STANDARD CURVE USING $^{125}$I-(SUCCINYL DIGOXIN TYROSINE METHYL ESTER) OF EXAMPLE VIII

EXAMPLE IX

Succinyl Digoxin Tyrosine

Ten mg of succinyl digoxin tyrosine methyl ester was suspended in 5 ml of 0.9% sodium chloride, 0.001% tetracycline hydrochloride and 5 ml of 0.05M phosphate buffer, pH7.6. The slurry was sonicated for five minutes, and 10 mg of chymotryksin was added. The reaction reaction, which was initially biphasic, was rotate mixed for 30 minutes in a 12 ml vial. The enzyme catalyzed hydrolysis yielded a soluble product, so that the reaction mixture became a clear solution. The solution was evaporated to dryness, and the residue was taken up in methanol. Insoluble material was separated by centrifugation, and the supernate was concentrated in vacuum. The product, succinyl digoxin tyrosine, was isolated by TLC on 50 × 80 × 0.25 mm layers of silica gel, using 1:3 methanol-chloroform. The succinyl digoxin tyrosine was eluted with 100% ethanol and diluted to give an O.P. of 0.100 at 278 mm. Analysis: $\lambda 1$ max = 278 nm (ethanol), $\lambda_2$ max = 222.5 nm; spectrum identical to succinyl digoxin tyrosine methyl ester and to a mixture of digoxin and TME (1:1 molar ratio); TLC, slower $R_f$ than succinyl digoxin tyrosine methyl ester, digoxin, succinyl digoxin or TME (1:3 methanol - chloroform).

EXAMPLE X

$^{125}$I-(Succinyl Digoxin Tyrosine)

To a 10 × 75 mm test tube which contained 75 µl of 0./5M pH 7.6 phosphate buffer and 25λ(6 mCi) of Na $^{125}$I was added 25λ(1.5 µg) of succinyl diogoxin tyrosine in ethanol solution. To the stirred solution was added 25 µl (100 µg) of chloramine T solution, and exactly two minutes later was added 25λ (100 µg) of sodium meta-bisulfite. The reaction solution was transferred to a vial containing 10 ml of deionized water and 1g of Amberlite IRA - 400 C.P. (chloride form) anion exchange resin. The vial was rotate mixed for five minutes, and the aqueous supernate was removed and discarded. The product was eluted from the resin by rotate mixing with 10 ml of 2% actic acid-98% ethanol for ten minutes. The supernate was diluted with 190 ml of 0.5% albumin, 0.9% sodium chloride, 0.0025% tetracycline hydrochloride to give 920 µCi of $^{125}$I-(succinyl digoxin tyrosine).

This radioactive derivative of digoxin had different nonspecific absorption properties from the ester form; for example, $^{125}$I-(succinyl digoxin tyrosine) gave 0.3% nonspecific binding to the insoluble constituents of the antibody polymer tablets as opposed to 1.6% with $^{125}$I-(succinyl digoxin tyrosine methyl ester). Therefore, it may prove better for some applications.

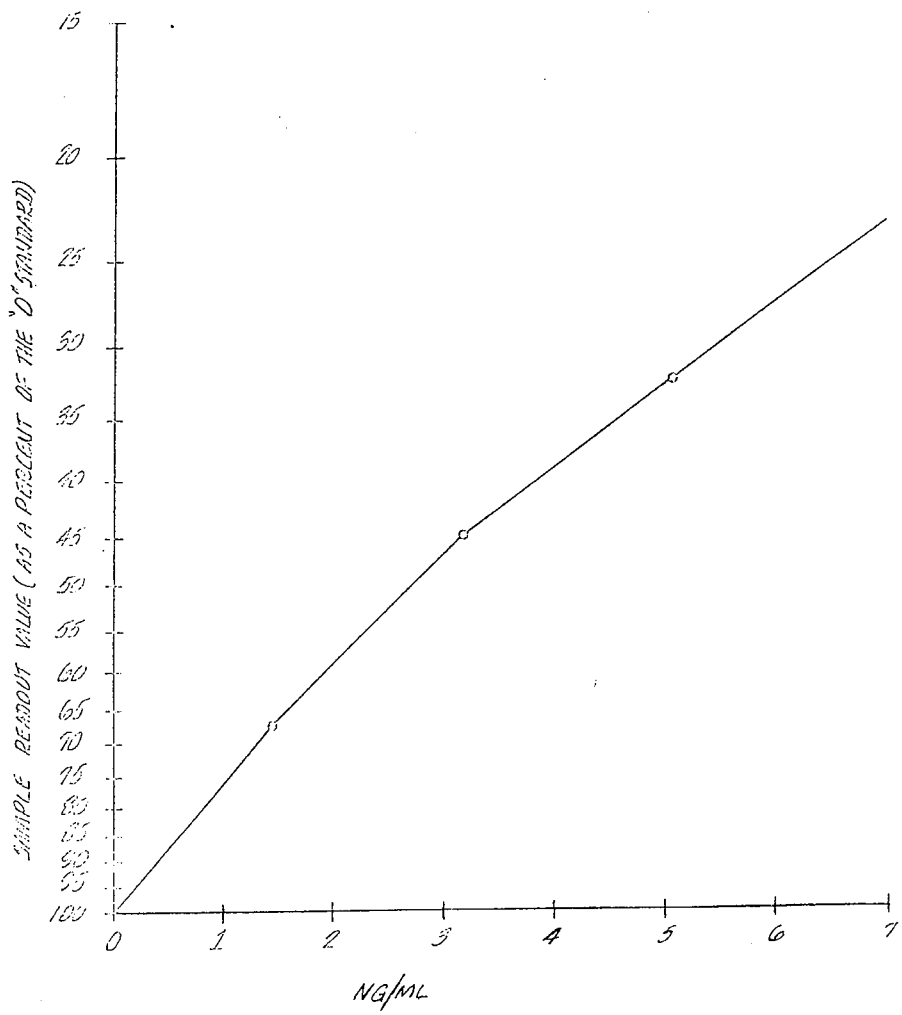

STANDARD CURVE USING $^{125}$I-(SUCCINYL DIGOXIN TYROSINE) PREPARED AS IN EXAMPLE X

EXAMPLE XI

Synthesis of $^{125}$I-(Succinyl Digoxin Tyrosine Methyl Ester) of High Purity To a 10 × 75 mm test tube which contained an 8 mm stirring bar was added 25λ(1.57 μg) of ethanolic succinyl digoxin tyrosine methyl ester, 75λ of 0.5M pH7.6 phosphate buffer, and 25 μl (6 mCi) of Na$^{125}$I solution. To the stirred solution was added 25λ of 0.4% chloramine T in 0.05M, pH 7.6 phosphate buffer. Exactly two minutes later was added 25λ of 0.4% sodium metabisulfite in 0.05M phosphate buffer, pH 7.6 The reaction solution was transferred to a vial which contained 1g of Amberlite IRA-400 C.P. (chloride form) anion exchange resin and 10 ml of deionized water. The vial was rotate mixed for five minutes, and then the supernate was removed and discarded. The desired product was eluted with 10 ml of 100% ethanol and diluted to 200 ml with 0.5% albumin, 0.9% sodium chloride, 0.0025% tetracycline hydrochloride to give 1.09 mCi of $^{125}$I-(succinyl digoxin tyrosine methyl ester).

EXAMPLE XII

A digoxin antibody is synthesized by the injection of an antigen having as its hapten portion digoxin into rabbits. The antibody is then processed into a polymer tablet, such procedures constituting no part of this invention. Radioactive digoxin $^{125}$I solutions as synthesized in Example VIII, the antibody tablet and lyophilized digoxin standards in human serum are used to determine an unknown quantity of digoxin in human serum. For a more detailed discussion of this procedure, see "Polymeric Competitive Protein Binding Absorbants for Radioassay," U.S. Ser. No. 412,918, filed Nov. 5, 1973 and assigned to the same assignee as the present invention.

5.0 ml of venous blood to be tested for digoxin is antiseptically transferred to a test tube. The blood is allowed to coagulate and the serum is separated from the clot by centrifugation. It should be noted that hemoloyzed serum cannot be used as a sample. The serum collected should be tested immediately or if not tested within 24 hours, frozen at −20°C. Storage for less than 24 hours may be under refrigeration at 4°-8°C.

The polymer antibody tablet is transferred to reaction/counting vials and into which is pipetted and gently mixed 0.5 ml of normal saline solution. The mixtures are allowed to stand for approximately 5 minutes to assure complete dissolution of the polymer tablets. Into different counting vials containing the dissolved polymer tablet is transferred 0.5 ml of serum sample and serum standards. The serums are gently mixed and allowed to stand for 10 minutes. Into each vial is then added 0.045 ml of $^{125}$I digoxin solution made in accordance with this invention, which is gently mixed with the serum/antibody slurry. The vials are incubated for 30 minutes at room temperature (15°–30°C). 5.0 ml of normal saline is mixed by vortex until the precipitate in the vials is suspended. The vials are then centrifuged at 3,000 rpm for approximately 5 minutes.

Immediately after centrifugation, the saline wash is carefully decanted, care being taken to avoid disturbing the small, packed precipitate. The precipitate is again washed, centrifuged and decanted with 5.0 ml of normal saline. The vials are then checked for radioactivity via any convenient method, as for example a scaler type gamma counter.

The known digoxin standards are plotted with the sample to be measured, and the digoxin content of the unknown serum is graphically interpolated.

The coefficient of variation using this procedure, for 192 samples of human serum pool was 3.5% (0.049 mg/ml) at a concentration of 1.4 mg/ml digoxin. The time to analyze 60 samples and three standards was approximately 1½ hours plus or minus 15 minutes.

What is claimed is:

1. A radioactive glycoside useful in radioimmunoassay of the formula:

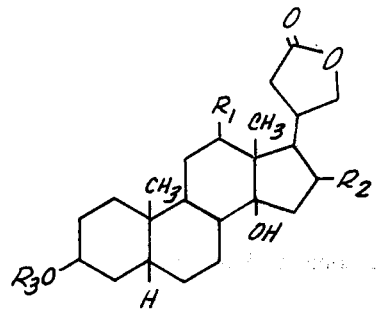

wherein $R_1$ and $R_2$ are selected from the group consisting of hydroxyl or hydrogen and $R_3$ is selected from the group consisting of mono-, di-, tri-, and tetrasaccharides bonded to an $^{125}$L-labeled substituent through a sugar hydroxyl group.

2. The compound of claim 1 wherein $R_3$ is a mono- or oligo- saccharide with monomeric constituents selected from the group consisting of rhamnose, antiarose, digitalose, thevetose, talomethylose, digitoxose, cymarose, oleandrose, sarmentose, boivinose, and diginose.

3. A radioactive glycoside useful in radioimmunoassay of the formula:

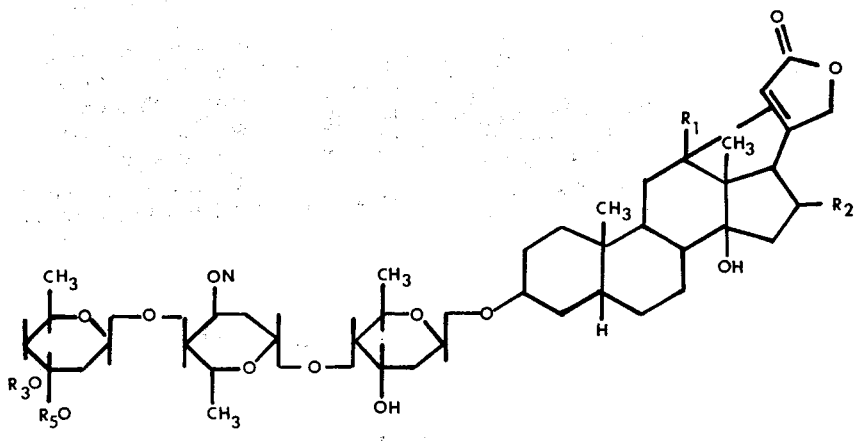

wherein $R_1$ and $R_2$ are H or OH, $R_4$ is glucose, hydrogen or X, and $R_5$ is hydrogen, acetyl or X, X being an $^{125}I$-substituted aromatic moiety conjugated to the glycoside chain via the condensation residue of a dicarboxylic acid, acid halide or acid anhydride, provided that one of $R_4$ or $R_5$ is X unless $R_4$ is glucose, in which case glucose is likewise conjugated to X.

4. The compound of claim 3 wherein the dicarboxylic acid derivative of the radioactive phenol bears a radioactive isotope ortho to the hydroxyl of the phenol ring.

5. The compound of claim 3 wherein the phenol is tyrosine or a tyrosine derivative.

6. The compound of claim 5 wherein the phenol is tyrosine methyl ester.

7. The compound of claim 3 wherein said residue is selected from the group consisting of succinyl, carbonyl, oxaloyl, malonyl, glutaryl, adipoyl, pimeloyl, maleyl or phthaloyl.

8. The compound of claim 3 wherein X is of the formula:

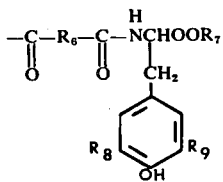

wherein $R_6$ is selected from the group consisting of $C_1$ to $C_6$ alkyl, vinylene, and phenylene, $R_7$ is selected from the group consisting of H and $C_1$ to $C_6$ alkyl, $R_8$ and $R_9$ are selected from the group consisting of H and $^{125}I$, at least one of $R_8$ and $R_9$ being $^{125}I$.

9. The compound $^{125}I$-(3'''-succinyl digoxin tyrosine methyl ester).

10. The compound $^{125}I$-(4'''succinyl digoxin tyrosine methyl ester).

11. The compound $^{125}I$-(3'''-succinyl digitoxin tyrosine methyl ester).

12. The compound $125I$-(4'''-succinyl digitoxin tyrosine methyl ester).

13. The compound $^{125}I$-(3'''-succinyl digoxin tyrosine).

14. The compound $^{125}I$-(4'''-succinyl digoxin tyrosine).

15. The compound $^{125}I$-(3'''-succinyl digitoxin tyrosine).

16. The compound $^{125}I$-(4'''-succinyl digitoxin tyrosine).

17. A process of synthesizing a radioactive glycoside useful for radioimmunoassay comprising the steps of reacting a steroid glycoside of the general formula:

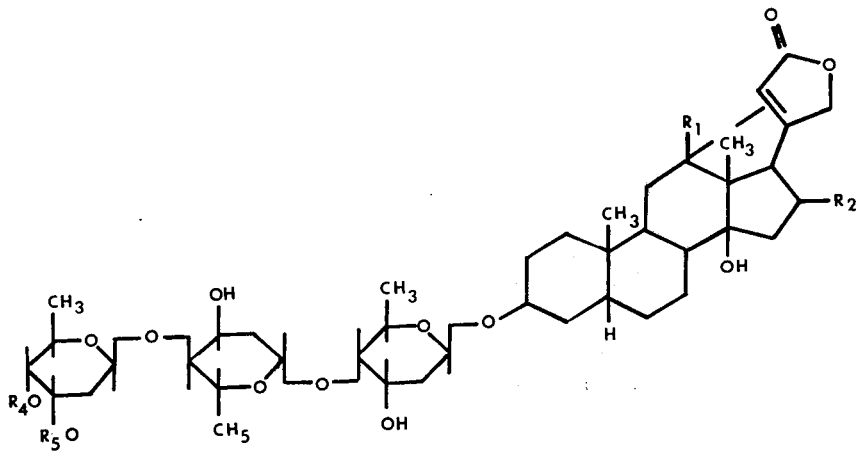

wherein $R_1$ and $R_2$ are selected from the group consisting of H or hydroxyl, $R_4$ is selected from the group consisting of H or glucose and $R_5$ is selected from the group consisting of hydrogen or acetyl with a reagent selected from the group consisting of a diacid, diacid anhydride or a diacidhalide to provide the corresponding dicarboxylic acid derivative conjugated at a sugar hydroxyl and further reacting the resulting dicarboxylic acid derivative with an aromatic moiety activated toward electrophilic substitution effecting electrophilic substitution of said moiety with $^{125}I$.

18. The process of claim 17 wherein the aromatic moiety selected from the group consisting of tyrosine or a tyrosine ester.

19. The process of claim 17 wherein the diacid or diacidanhydride is selected from the group consisting of succinnic acid, glutaric acid, succinic anhydride or glutaric anhydride.

20. The compound of claim 3 wherein said aromatic moiety is a phenol.

21. The compound of claim 20 wherein $^{125}I$ is ortho to the hydroxy substituent of the phenol ring.

* * * * *

UNITED STATES PATENT AND TRADEMARK OFFICE
CERTIFICATE OF CORRECTION

PATENT NO. : 3,963,697
DATED : June 15, 1976
INVENTOR(S) : Robert F. Coombes

It is certified that error appears in the above-identified patent and that said Letters Patent are hereby corrected as shown below:

The structural formula in Claim 3 should read:

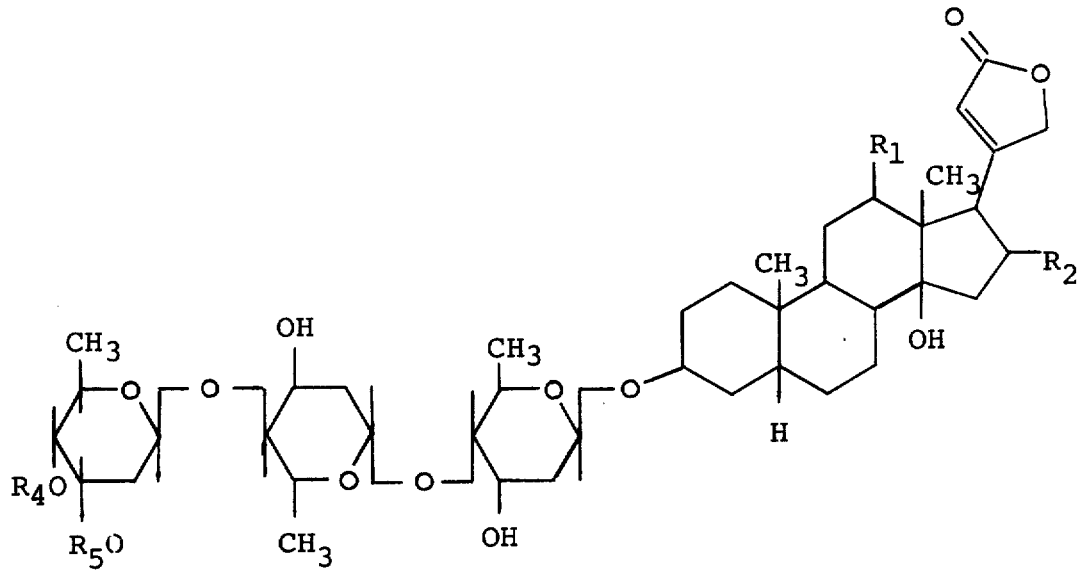

UNITED STATES PATENT AND TRADEMARK OFFICE
CERTIFICATE OF CORRECTION

PATENT NO. : 3,963,697
DATED : June 15, 1976
INVENTOR(S) : Robert F. Coombes

It is certified that error appears in the above-identified patent and that said Letters Patent are hereby corrected as shown below:

In the structural formula at the bottom of Column 6, the portion reading

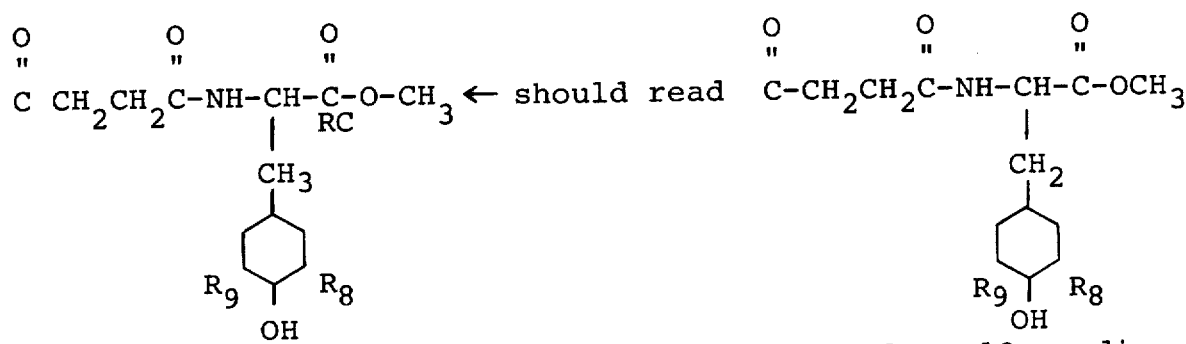

That portion of Claim 1 at line 46 of column 18 reading "$125_L$-labeled" should read -- $125_I$-labeled --.

UNITED STATES PATENT AND TRADEMARK OFFICE
CERTIFICATE OF CORRECTION

PATENT NO. : 3,963,697
DATED : June 15, 1976
INVENTOR(S) : Robert F. Coombes

It is certified that error appears in the above-identified patent and that said Letters Patent are hereby corrected as shown below:

The structural formula of Claim 8 should read:

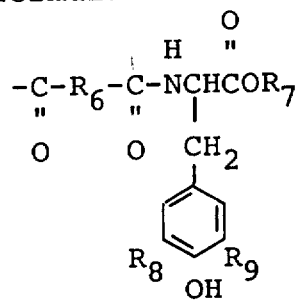

That portion of Claim 12 at line 5 of column 20 reading 125I-" should read -- $^{125}$I- --.

The structural formula of Claim 17 should read:

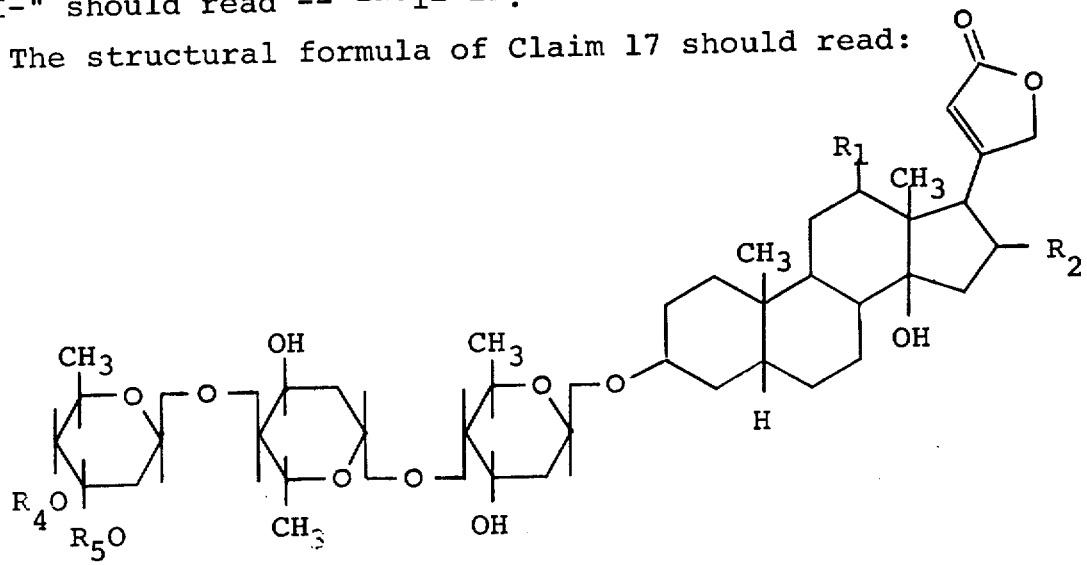

UNITED STATES PATENT AND TRADEMARK OFFICE
CERTIFICATE OF CORRECTION

PATENT NO. : 3,963,697
DATED : June 15, 1976
INVENTOR(S) : Robert F. Coombes

It is certified that error appears in the above-identified patent and that said Letters Patent are hereby corrected as shown below:

In the structural formula between lines 15 and 34 of Columns 1 and 2, the portion reading 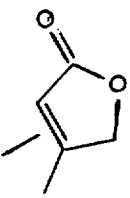 should read 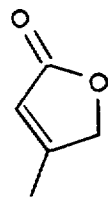 .

In the structural formula in Column 5, the portion reading should read

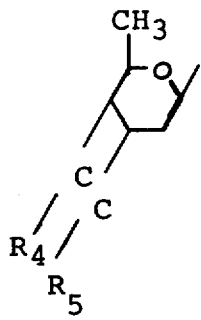 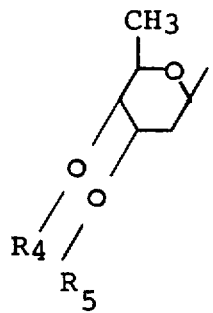

Signed and Sealed this

Third Day of May 1977

[SEAL]

Attest:

RUTH C. MASON
Attesting Officer

C. MARSHALL DANN
Commissioner of Patents and Trademarks